(12) United States Patent
Ohta et al.

(10) Patent No.: US 7,935,931 B2
(45) Date of Patent: May 3, 2011

(54) RADIATION IMAGE CAPTURING SYSTEM

(75) Inventors: Yasunori Ohta, Yokohama (JP); Eiichi Kito, Minami-ashigara (JP); Tsuyoshi Tanabe, Odawara (JP); Takuya Yoshimi, Yokohama (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/654,257

(22) Filed: Dec. 15, 2009

(65) Prior Publication Data

US 2010/0156593 A1    Jun. 24, 2010

Related U.S. Application Data

(63) Continuation-in-part of application No. 12/222,502, filed on Aug. 11, 2008, now Pat. No. 7,655,916.

(30) Foreign Application Priority Data

Aug. 10, 2007  (JP) .................................. 2007-209030
Jun. 25, 2008  (JP) .................................. 2008-165207

(51) Int. Cl.
*H01L 27/146* (2006.01)
(52) U.S. Cl. ................................................. 250/370.08
(58) Field of Classification Search .......... 250/370.01–370.15; 378/98.8
See application file for complete search history.

(56) References Cited

U.S. PATENT DOCUMENTS

| 7,203,278 | B2* | 4/2007 | Wendt et al. ............... 378/98.8 |
| 7,298,825 | B2 | 11/2007 | Omernick et al. |
| 7,324,628 | B2 | 1/2008 | Liu et al. |
| 7,359,482 | B2* | 4/2008 | Schmitt .................... 378/98.8 |
| 7,365,337 | B2 | 4/2008 | Tsuchino et al. |
| 7,426,261 | B2 | 9/2008 | Spahn |
| 7,474,731 | B2 | 1/2009 | Spahn |
| 2003/0223540 | A1 | 12/2003 | Hayashida et al. |
| 2007/0015476 | A1 | 1/2007 | Attar et al. |

FOREIGN PATENT DOCUMENTS

| JP | 07-140255 | 6/1995 |
| JP | 2000-105297 | 4/2000 |
| JP | 2006-263339 | 10/2006 |

* cited by examiner

*Primary Examiner* — David P Porta
*Assistant Examiner* — Kiho Kim
(74) *Attorney, Agent, or Firm* — Jean C. Edwards, Esq.; Akerman Senterfitt LLP

(57) ABSTRACT

The power consumption of a battery for supplying electric power to a cassette having a radiation detector for detecting radiation image information is greatly reduced. When a cassette transceiver of the cassette starts transmitting the radiation image information to a console transceiver of a console, the cassette transceiver changes the gain of a variable-gain amplifier to change a transmission radio-wave intensity, and transmits a test signal at the changed transmission radio-wave intensity. When the console transceiver receives the test signal, the console transceiver transmits a reception acknowledgement signal generated by a reception acknowledgement signal generator. In response to the reception acknowledgement signal, the cassette transceiver sets its own transmission radio-wave intensity to a value at the time the cassette transceiver received the reception acknowledgement signal, and transmits the radiation image information at the set transmission radio-wave intensity.

7 Claims, 10 Drawing Sheets

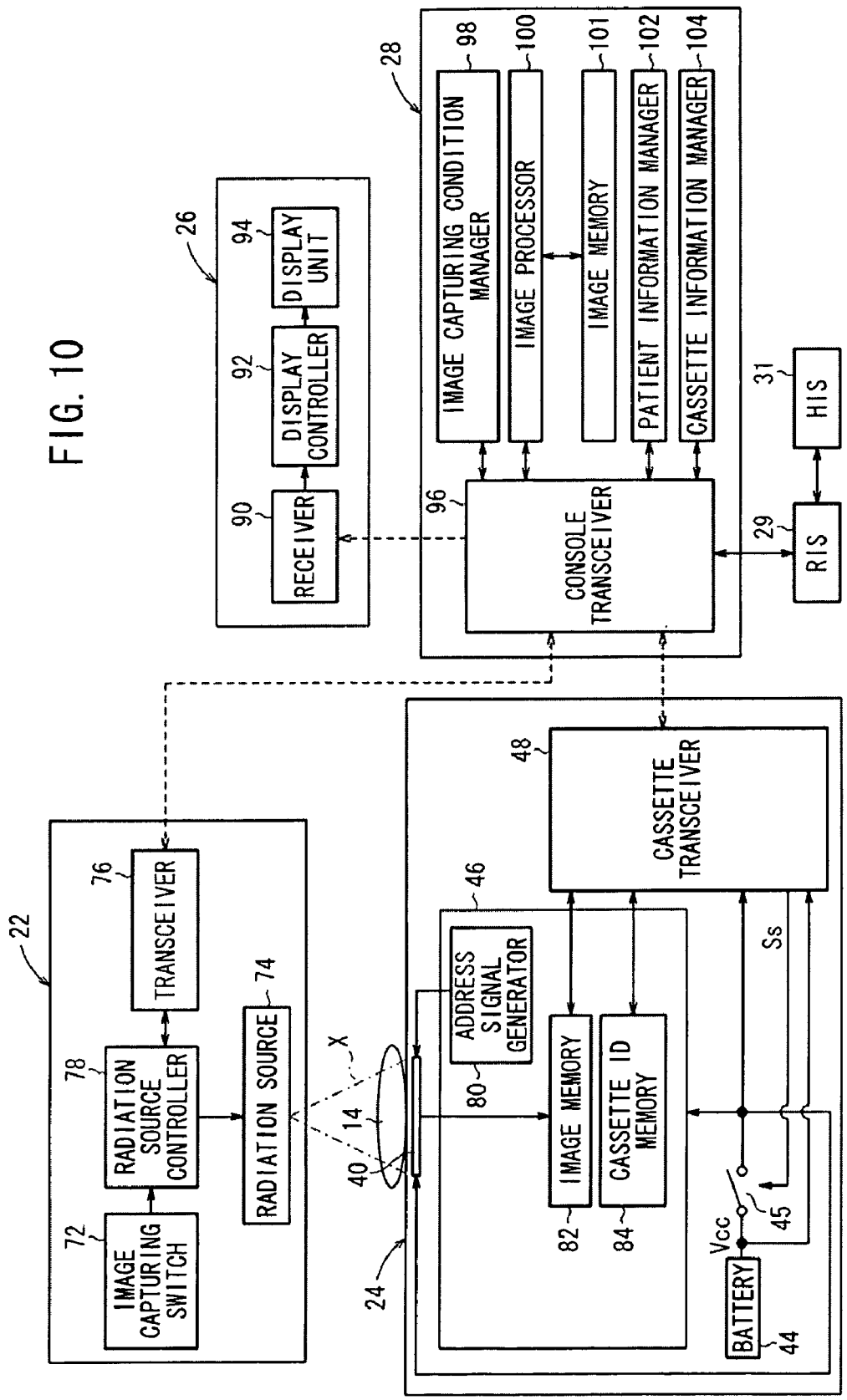

RADIATION IMAGE CAPTURING SYSTEM

CROSS-REFERENCE TO RELATED APPLICATIONS

This application is a Continuation-In-Part application of U.S. patent application Ser. No. 12/222,502, filed Aug. 11, 2008, now U.S. Pat. No. 7,655,916 and claims priority under 35 USC 119 from Japanese Patent Application Nos. 2007-209030, filed Aug. 10, 2007, and 2008-165207, filed Jun. 25, 2008, the contents of which are incorporated herein by reference in their entirety.

BACKGROUND OF THE INVENTION

1. Field of the Invention

The present invention relates to a radiation image capturing system having a cassette including a radiation detector for detecting a radiation that has passed through a subject and converting the detected radiation into radiation image information, and an external controller for receiving the radiation image information transmitted from the cassette.

2. Description of the Related Art

In the medical field, there have widely been used radiation image capturing apparatus which apply a radiation to a subject and guide the radiation that has passed through the subject to a radiation detector, which captures a radiation image from the radiation. Known forms of the radiation detector include a conventional radiation film for recording a radiation image by way of exposure, and a stimulable phosphor panel for storing a radiation energy representing a radiation image in a phosphor and reproducing the radiation image as stimulated light by applying stimulating light to the phosphor. The radiation film with the recorded radiation image is supplied to a developing device to develop the radiation, or the stimulable phosphor panel is supplied to a reading device to read the radiation image as a visible image.

In the operating room or the like, it is necessary to read a recorded radiation image immediately from a radiation detector after the radiation image is captured for the purpose of quickly and appropriately treating the patient. As a radiation detector which meets such a requirement, there has been developed a radiation detector having a solid-state detector for converting a radiation directly into an electric signal or converting a radiation into visible light with a scintillator and then converting the visible light into an electric signal to read a detected radiation image.

Radiation image capturing systems with such a radiation detector are disclosed in Japanese Patent No. 3494683 and Japanese Laid-Open Patent Publication No. 2006-263339.

According to Japanese Patent No. 3494683, radiation image information detected by a radiation detector is transmitted to a processor by way of wireless communications, and is processed by the processor.

Japanese Laid-Open Patent Publication No. 2006-263339 discloses an electronic cassette capable of transmitting radiation image information at high frequencies in excess of 1 GHz for high-speed transmission of a large amount of image data.

However, the electronic cassette consumes a large amount of electric power in transmitting radiation image information to an external source by way of wireless communications. Therefore, a large-size battery is needed to energize the electronic cassette, and hence the electronic cassette becomes large in volume and weight.

SUMMARY OF THE INVENTION

It is an object of the present invention to provide a radiation image capturing system which consumes a reduced amount of electric power in transmitting radiation image information from a cassette to an external source by way of wireless communications, thereby saving electric power of a battery.

A radiation image capturing system according to the present invention comprises a cassette comprising a radiation detector for detecting a radiation having passed through a subject and converting the detected radiation into radiation image information, an image memory for storing the converted radiation image information, a first transceiver for changing a transmission radio-wave intensity at which a test signal or the radiation image information stored in the image memory is transmitted to an external source by way of wireless communications, and a battery for supplying electric power to the radiation detector and the first transceiver, and an external controller comprising a second transceiver for receiving the test signal and the radiation image information transmitted from the cassette and transmitting a reception acknowledgement signal to the first transceiver, wherein when the first transceiver of the cassette starts transmitting the radiation image information to the second transceiver of the external controller, the first transceiver transmits the test signal while changing the transmission radio-wave intensity, and when the second transceiver receives the test signal, the second transceiver transmits the reception acknowledgement signal, and in response to the reception acknowledgement signal, the first transceiver sets a transmission radio-wave intensity of its own to a value at the time the first transceiver received the reception acknowledgement signal, and transmits the radiation image information at the set transmission radio-wave intensity.

According to the present invention, when the first transceiver of the cassette starts transmitting the radiation image information to the second transceiver of the external controller, the first transceiver transmits the test signal while changing the transmission radio-wave intensity, and when the second transceiver receives the test signal, the second transceiver transmits the reception acknowledgement signal, and in response to the reception acknowledgement signal, the first transceiver sets a transmission radio-wave intensity of its own to a value at the time the first transceiver received the reception acknowledgement signal, and transmits the radiation image information at the set transmission radio-wave intensity. Consequently, the power consumption required to transmit the radiation image information from the first transceiver to the second transceiver is minimized, and, as a result, the electric power stored in the battery of the cassette is saved.

When the first transceiver receives the reception acknowledgement signal, the first transceiver may set a transmission radio-wave intensity of its own to a value which represents the sum of the transmission radio-wave intensity at the time the first transceiver received the reception acknowledgement signal and a predetermined value, and may transmit the radiation image information at the set transmission radio-wave intensity. Therefore, the first transceiver can transmit the radiation image information stably and reliably while saving the electric power stored in the battery.

The cassette may further comprise a power switch, and the first transceiver may transmit the test signal when the power switch is turned on. When the power switch is turned on, it is highly likely to capture a radiation image from then on. As the transmission radio-wave intensity is set to a minimum required when the radiation image is captured, the radiation image information can reliably be transmitted to the external controller while minimizing the power consumption of the battery.

The cassette may turn off the power switch when the first transceiver finishes transmitting the radiation image information with the power switch being turned on. The electric power stored in the battery is thus further saved.

According to the present invention, since the power consumption required to transmit the radiation image information from the cassette to the external controller by way of wireless communications can be reduced, the electric power stored in the battery which energizes the cassette is saved.

The above and other objects, features, and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 10 is another block diagram of the radiation image capturing system.

DESCRIPTION OF THE PREFERRED EMBODIMENTS

Figure 1:
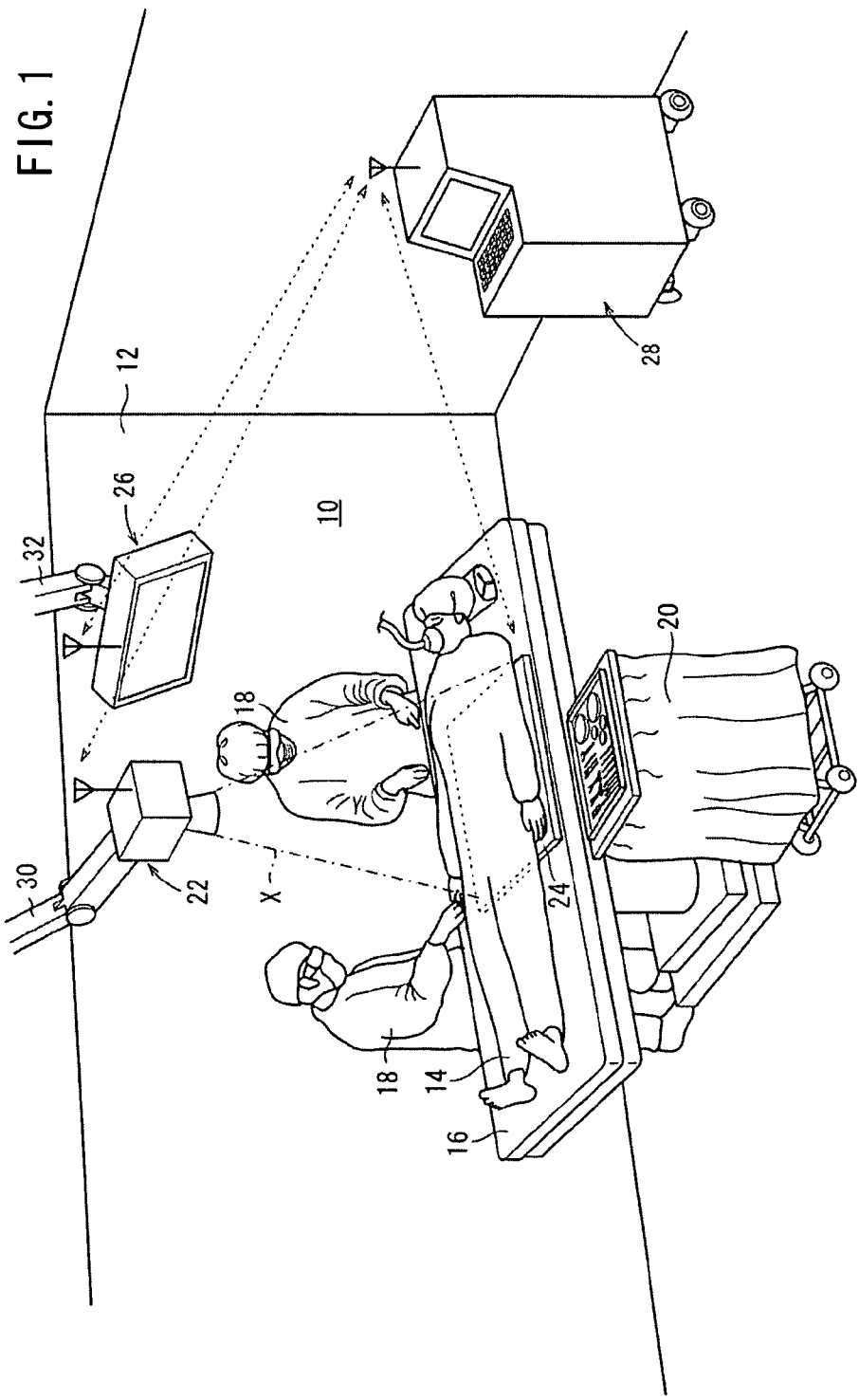
FIG. 1 is a perspective view of an operating room incorporating a radiation image capturing system according to an embodiment of the present invention.

As shown in FIG. 1, an operating room 12 incorporates a radiation image capturing system 10 according to a preferred embodiment of the present invention. The operating room 12 has, in addition to the radiation image capturing system 10, a surgical table 16 for a patient 14 to lie thereon, and an instrument table 20 disposed on one side of the surgical table 16 for placing thereon various tools and instruments to be used by surgeons 18 for operating the patient 14. The surgical table 16 is surrounded by various apparatus required for surgical operations, including an anesthesia apparatus, an aspirator, an electrocardiograph, a blood pressure monitor, etc.

The radiation image capturing system 10 includes an image capturing apparatus 22 for irradiating the patient 14 as a subject with a radiation X at a dose according to image capturing conditions, a cassette (radiation detecting cassette) 24 housing therein a radiation detector, to be described later, for detecting the radiation X that has passed through the patient 14, a display device 26 for displaying a radiation image based on the radiation X that is detected by the radiation detector, and a console (an external controller for the cassette 24) 28 for controlling the image capturing apparatus 22, the cassette 24, and the display device 26. The console 28, the image capturing apparatus 22, the cassette 24, and the display device 26 send and receive signals by way of wireless communications indicated by the broken lines.

The image capturing apparatus 22 is coupled to a universal arm 30 so as to be movable to a desired position for capturing a desired area of the patient 14 and also to be retractable to a position out of the way while the surgeons 18 are performing a surgical operation on the patient 14. Similarly, the display device 26 is coupled to a universal arm 32 so as to be movable to a position where the surgeons 18 can easily confirm a captured radiation image displayed on the display device 26.

Figure 2:
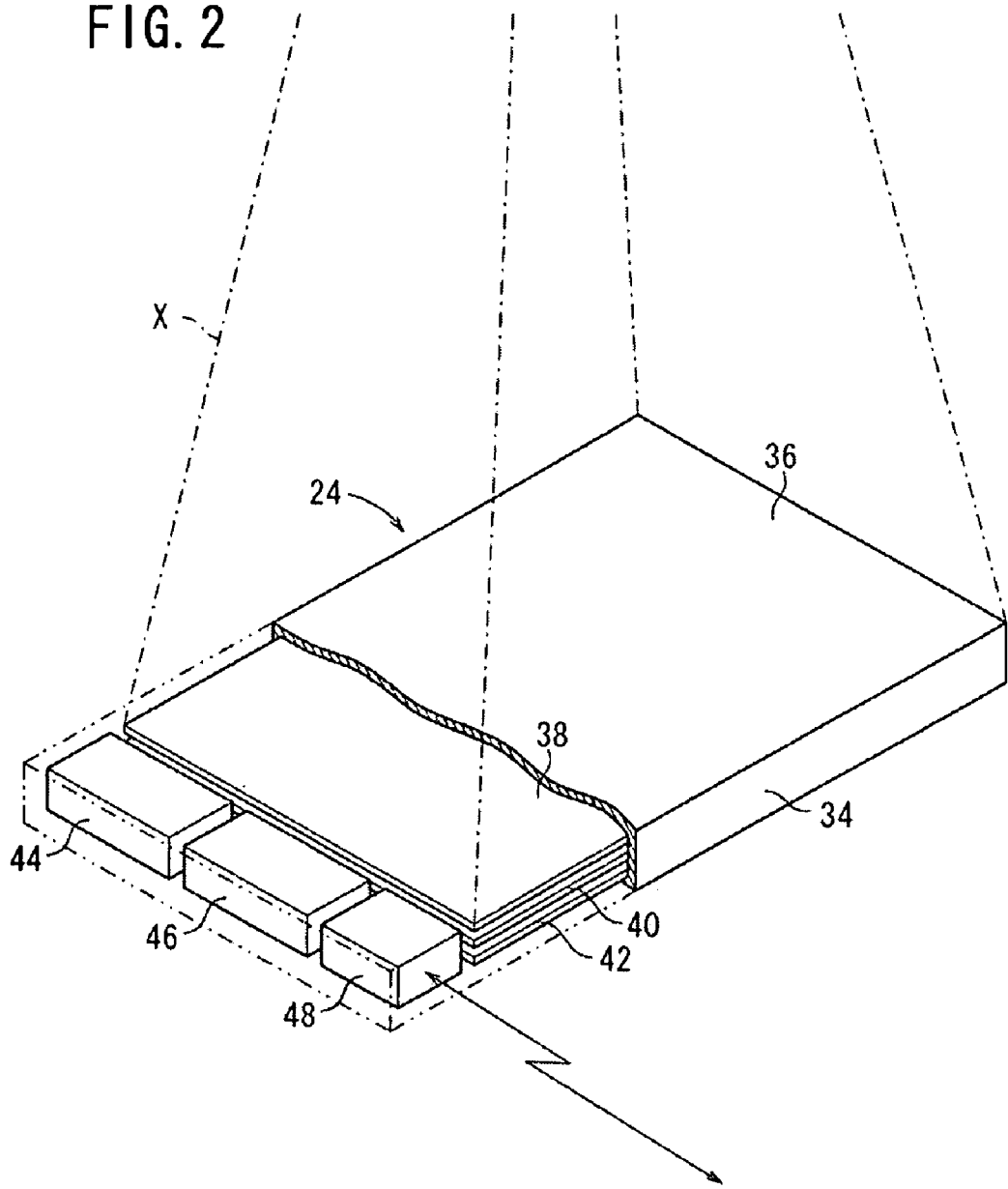
FIG. 2 is a perspective view, partly cut away, showing internal structural details of a radiation detecting cassette according to the present invention.

FIG. 2 shows in perspective internal structural details of the cassette 24. As shown in FIG. 2, the cassette 24 has a casing 34 made of a material permeable to the radiation X. The casing 34 houses therein a grid 38 for removing scattered rays of the radiation X from the patient 14, a radiation detector 40 for detecting the radiation X that has passed through the patient 14, and a lead plate 42 for absorbing back scattered rays of the radiation X, which are successively arranged in the order named from a surface 36 of the casing 34 which is irradiated with the radiation X. The irradiated surface 36 of the casing 34 may be constructed as the grid 38.

The casing 34 also houses therein a battery 44 as a power supply of the radiation detecting cassette 24, the battery 44 having a voltage Vcc, a cassette controller 46 for energizing the radiation detector 40 with electric power supplied from the battery 44, and a cassette transceiver (first transceiver) 48 for sending and receiving signals including the information of the radiation X detected by the radiation detector 40, to and from the console 28. A shield plate of lead or the like should preferably be placed over the side surfaces of the cassette controller 46 and the transceiver 48 under the irradiated surface 36 of the casing 34 to protect the cassette controller 46 and the transceiver 48 against damage which would otherwise be caused if irradiated with the radiation X.

Figure 3:
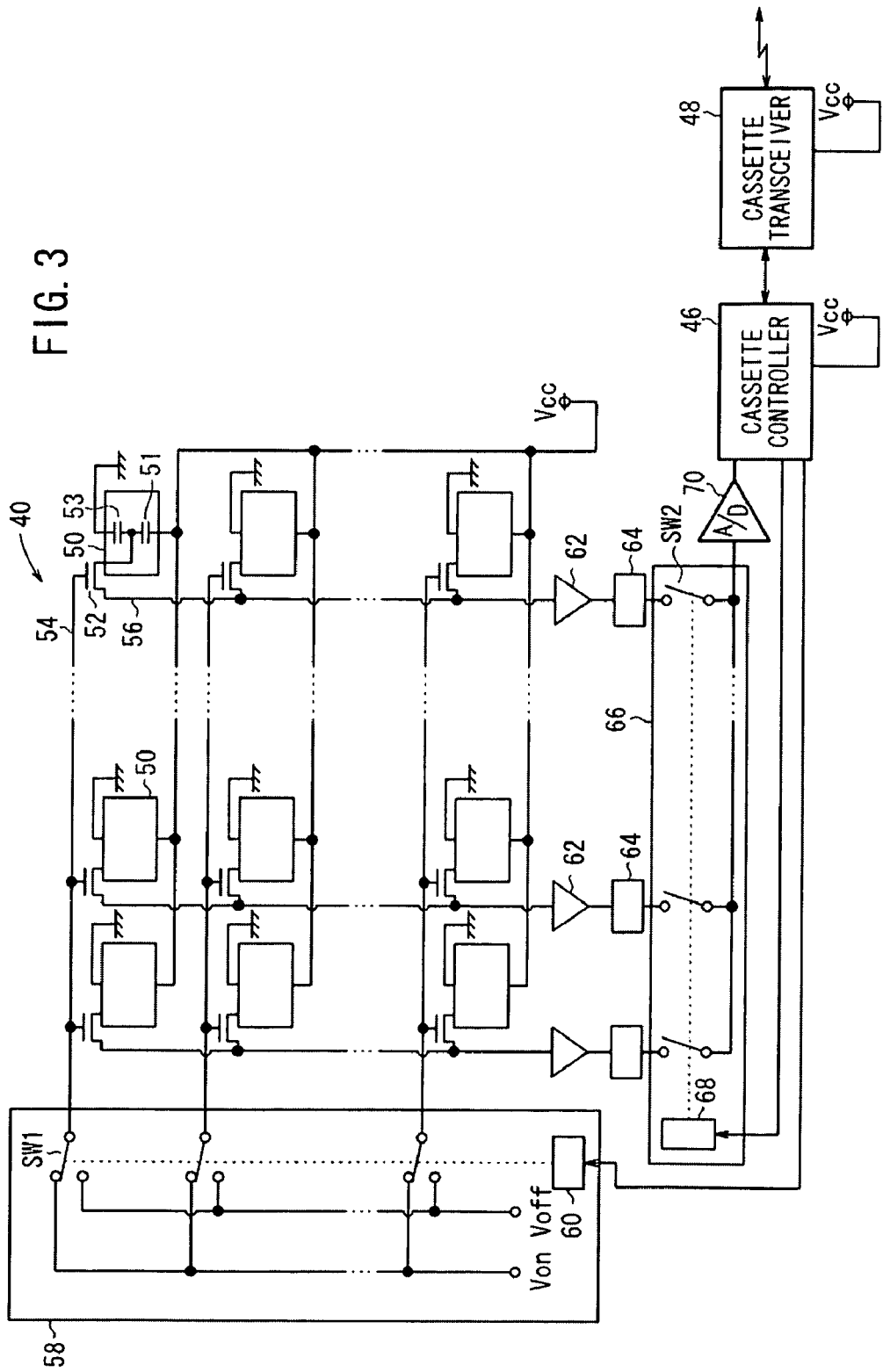
FIG. 3 is a block diagram of a circuit arrangement of a radiation detector of the radiation detecting cassette shown in FIG. 2.

FIG. 3 shows in block form a circuit arrangement of the radiation detector 40. As shown in FIG. 3, the radiation detector 40 comprises an array of thin-film transistors (TFTs) 52 arranged in rows and columns, a photoelectric conversion layer 51 made of a material such as amorphous selenium (a-Se) for generating electric charges upon detection of the radiation X, the photoelectric conversion layer 51 being disposed on the array of TFTs 52, and an array of storage capacitors 53 connected to the photoelectric conversion layer 51. When the radiation X is applied to the radiation detector 40, the photoelectric conversion layer 51 generates electric charges, and the storage capacitors 53 store the generated electric charges. Then, the TFTs 52 are turned on along each row at a time to read the electric charges from the storage capacitors 53 as an image signal. In FIG. 3, the photoelectric conversion layer 51 and one of the storage capacitors 53 are shown as a pixel 50, and the pixel 50 is connected to one of the TFTs 52. Details of the other pixels 50 are omitted from illustration. Since amorphous selenium tends to change its structure and lose its function at high temperatures, it needs to be used in a certain temperature range. Therefore, some means for cooling the radiation detector 40 should preferably be provided in the cassette 24.

The TFTs 52 connected to the respective pixels 50 are connected to respective gate lines 54 extending parallel to the rows and respective signal lines 56 extending parallel to the columns. The gate lines 54 are connected to a line scanning driver 58, and the signal lines 56 are connected to a multiplexer 66 serving as a reading circuit.

The gate lines 54 are supplied with control signals Von, Voff for turning on and off the TFTs 52 along the rows from the line scanning driver 58. The line scanning driver 58 comprises a plurality of switches SW1 for switching between the gate lines 54 and an address decoder 60 for outputting a selection signal for selecting one of the switches SW1 at a time. The address decoder 60 is supplied with an address signal from the cassette controller 46.

The signal lines 56 are supplied with electric charges stored in the storage capacitors 53 of the pixels 50 through the TFTs 52 arranged in the columns. The electric charges supplied to the signal lines 56 are amplified by amplifiers 62 connected respectively to the signal lines 56. The amplifiers 62 are connected through respective sample and hold circuits 64 to the multiplexer 66. The multiplexer 66 comprises a plurality of switches SW2 for successively switching between the signal lines 56 and an address decoder 68 for outputting a selection signal for selecting one of the switches SW2 at a time. The address decoder 68 is supplied with an address signal from the cassette controller 46. The multiplexer 66 has an output terminal connected to an A/D converter 70. A radiation image signal generated by the multiplexer 66 based on the electric charges from the sample and hold circuits 64 is converted by the A/D converter 70 into a digital image signal representing radiation image information, which is supplied to the cassette controller 46.

Figure 4:
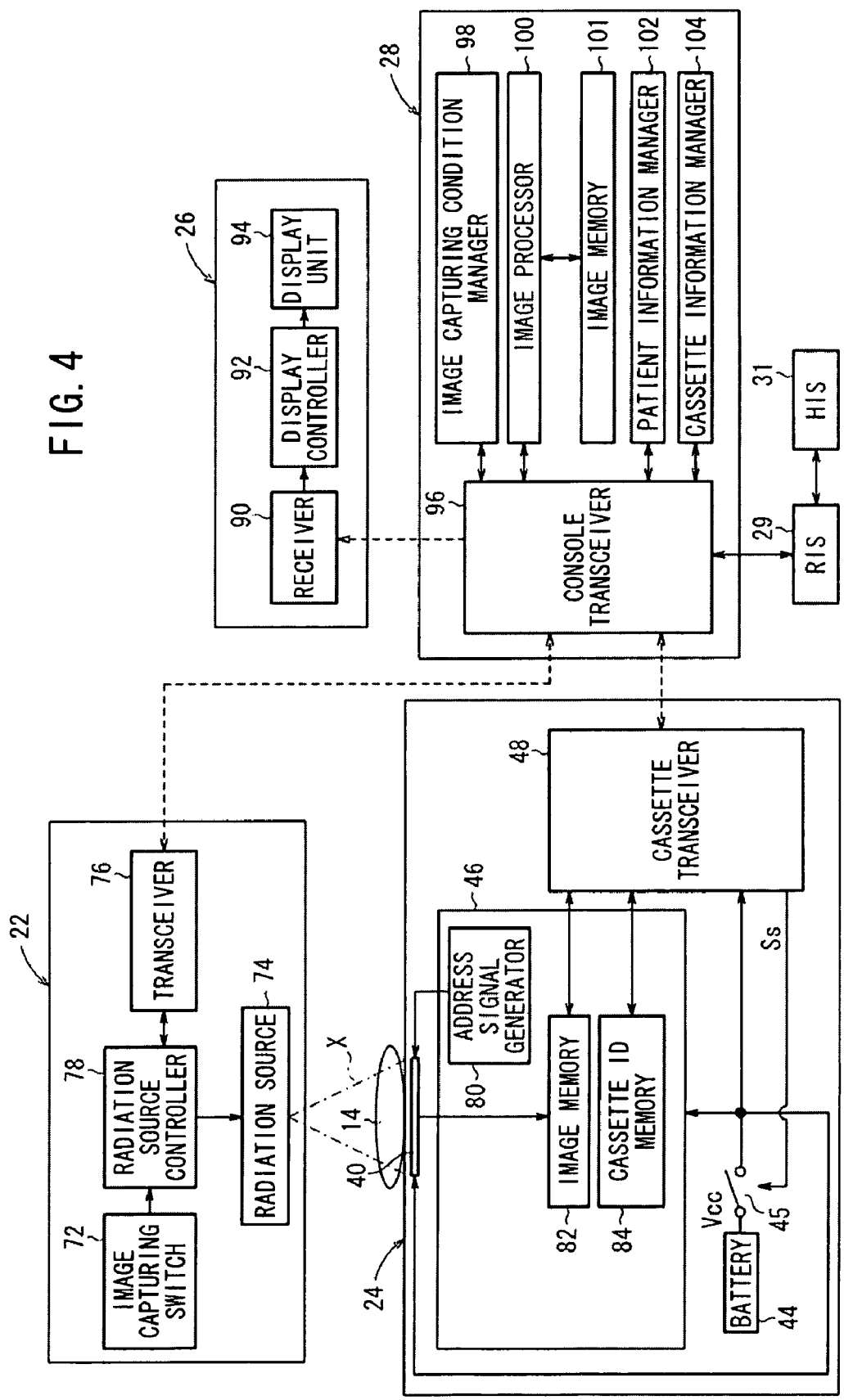
FIG. 4 is a block diagram of the radiation image capturing system shown in FIG. 1.

FIG. 4 shows in block form the radiation image capturing system 10 which comprises the image capturing apparatus 22, the cassette 24, the display device 26, and the console 28. The console 28 is connected to a radiology information system (RIS) 29 which generally manages radiation image information handled by the radiological department of the hospital and other information. The RIS 29 is connected to a hospital information system (HIS) 31 which generally manages medical information in the hospital.

The image capturing apparatus 22 comprises an image capturing switch 72, a radiation source 74 for outputting the radiation X, a transceiver 76 for receiving image capturing conditions from the console 28 by way of wireless communications and transmitting an image capturing completion signal, etc. to the console 28 by way of wireless communications, and a radiation source controller 78 for controlling the radiation source 74 based on an image capturing start signal supplied from the image capturing switch 72 and image capturing conditions supplied from the transceiver 76.

The cassette 24 houses therein the radiation detector 40, the battery 44, the cassette controller 46, the cassette transceiver 48, and a power switch 45. The power switch 45 is turned on and off manually or by a switch control signal Ss from the cassette transceiver 48, for selectively supplying electric power from the battery 44 to the radiation detector 40, the cassette controller 46, and the cassette transceiver 48. The cassette controller 46 comprises an address signal generator 80 for supplying address signals to the address decoder 60 of the line scanning driver 58 and the address decoder 68 of the multiplexer 66 of the radiation detector 40, an image memory 82 for storing the radiation image information detected by the radiation detector 40, a cassette ID memory 84 for storing cassette ID information for identifying the cassette 24, and an image compressor (amount-of-information reducing means), not shown, for compressing the radiation image information stored in the image memory 82 to reduce the amount of the radiation image information.

The cassette transceiver 48 receives a reception acknowledgement signal, to be described later, from the console 28 by way of wireless communications and transmits the cassette ID information stored in the cassette ID memory 84 and the radiation image information stored in the image memory 82 to the console 28 by way of wireless communications.

The display device 26 comprises a receiver 90 for receiving the radiation image information from the console 28, a display controller 92 for controlling the display of the received radiation image information, and a display unit 94 for displaying the radiation image information processed by the display controller 92.

The console 28 comprises a console transceiver (second transceiver) 96 for transmitting and receiving necessary information including radiation image information to and from the image capturing apparatus 22, the cassette 24, and the display device 26 by way of wireless communications, an image capturing condition manager 98 for managing image capturing conditions required for the image capturing apparatus 22 to capture radiation images, an image processor (image processing means) 100 for processing radiation image information transmitted from the cassette 24, an image memory 101 for storing the radiation image information processed by the image processor 100, a patient information manager 102 for managing patient information of the patient 14 whose images are to be captured, and a cassette information manager 104 for managing cassette information transmitted from the cassette 24.

The console 28 may be located outside of the operating room 12 insofar as it can transmit and receive signals to and from the image capturing apparatus 22, the cassette 24, and the display device 26 by way of wireless communications.

The image capturing conditions refer to condition for determining a tube voltage, a tube current, an irradiation time, etc. required to apply a radiation X at an appropriate dose to an area to be imaged of the patient 14. The image capturing conditions may include an area to be imaged of the patient 14, an image capturing method, etc., for example. The patient information refers to information for identifying the patient 14, such as the name, gender, patient ID number, etc. of the patient 14. Ordering information for ordering the capture of an image, including the image capturing conditions and the patient information can be set directly on the console 28 or can be supplied from an external source to the console 28 via the RIS 29. The cassette information refers to cassette ID information for identifying the cassette 24.

Figure 5:
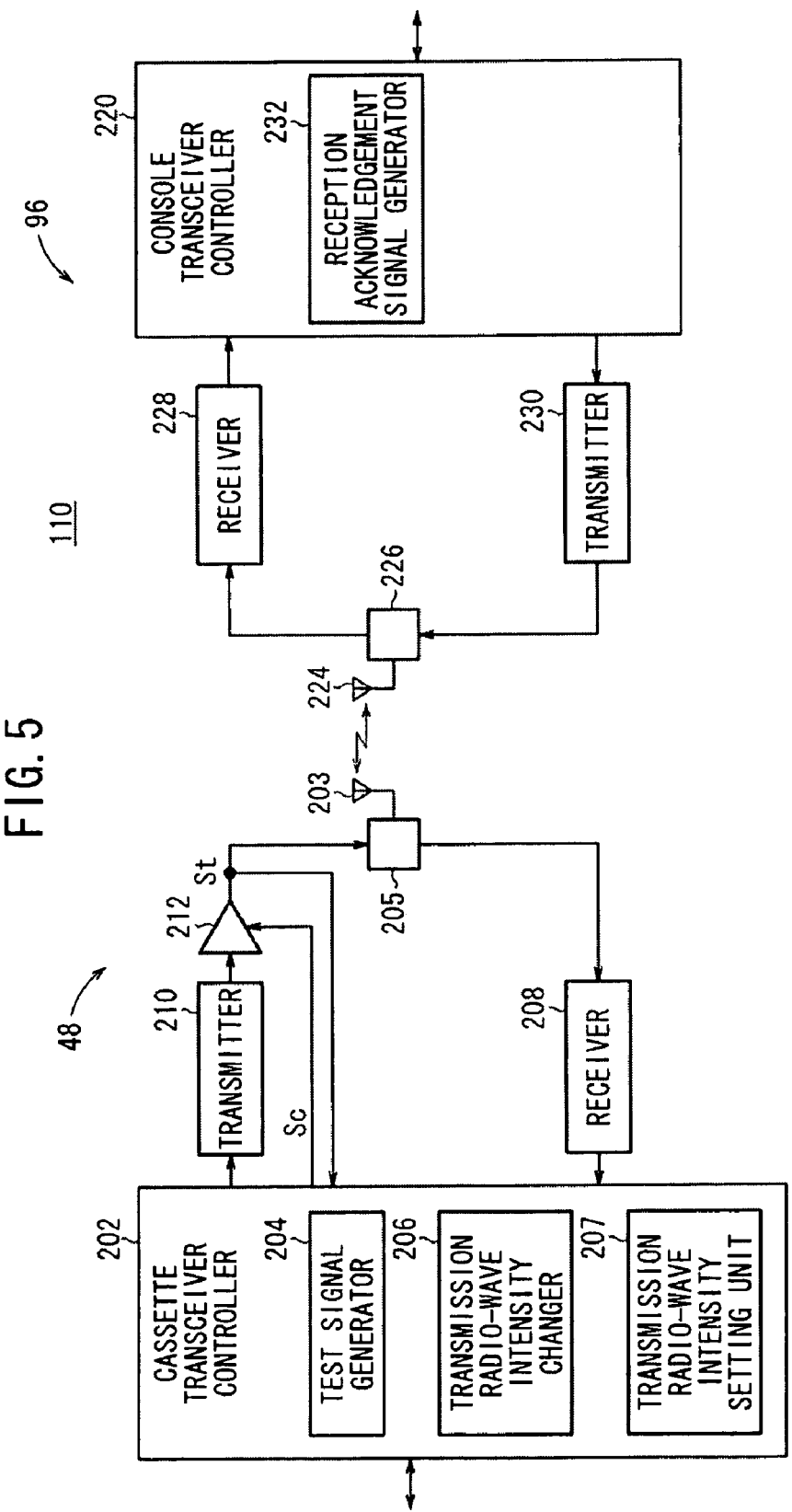
FIG. 5 is a block diagram of a radiation image information transmitting and receiving system as part of the radiation image capturing system according to the embodiment of the present invention.

FIG. 5 shows in block form a radiation image information transmitting and receiving system 110 as part of the cassette transceiver 48 and the console transceiver 96.

As shown in FIG. 5, the cassette transceiver 48 comprises a cassette transceiver controller 202 having a microcomputer, an antenna 203, an antenna sharing unit 205, a receiver 208, a transmitter 210, and a variable-gain amplifier 212.

The cassette transceiver controller 202 comprises a test signal generator 204, a transmission radio-wave intensity changer 206, and a transmission radio-wave intensity setting unit 207.

The receiver 208 receives a radio wave (RF (radio-frequency) signal) received by the antenna 203 through the antenna sharing unit 205, converts the received RF signal into an intermediate-frequency (IF) signal, demodulates the IF signal, and outputs the demodulated signal as reception data to the cassette transceiver controller 202. The transmitter 210 modulates data (radiation image information) read from the image memory 82 (see FIG. 4) or a test signal output from the test signal generator 204, and converts the modulated signal from an IF signal into an RF signal.

The test signal generator 204 supplies a test signal to the transmitter 210 at the time it detects when the power switch 45 is turned on.

The transmission radio-wave intensity changer 206 outputs a variable-gain control signal Sc to a control signal port of the variable-gain amplifier 212. The variable-gain control signal Sc enables the variable-gain amplifier 212 to amplify the test signal output from the transmitter 210 into a transmission signal St (proportional to a transmission radio wave) which is of a value increased stepwise from a minimum value.

As described later, when the power switch 45 is turned on, the transmission radio-wave intensity setting unit 207 stores the variable-gain control signal Sc for achieving the radio-wave intensity of the transmission signal St (proportional to a transmission radio wave) which has been determined by the transmission radio-wave intensity changer 206.

The transmission signal St is supplied through the antenna sharing unit 205 to the antenna 203, which transmits the transmission signal St as a transmission ratio wave.

The console transceiver 96 comprises a console transceiver controller 220 having a microcomputer, an antenna 224, an antenna sharing unit 226, a receiver 228, and a transmitter 230.

The console transceiver controller 220 has a reception acknowledgement signal generator 232. The receiver 228 receives a radio wave (RF signal) received by the antenna 224 through the antenna sharing unit 226, converts the received RF signal into an intermediate-frequency (IF signal) signal, demodulates the IF signal, and outputs the demodulated signal as reception data to the console transceiver controller 220. The demodulated reception data include a test signal or radiation image information.

When the reception acknowledgement signal generator 232 receives the test signal, it generates a reception acknowledgement signal and supplies the reception acknowledgement signal through the transmitter 230 and the antenna sharing unit 205 to the antenna 224, which transmits the reception acknowledgement signal as a radio wave.

Figure 6:
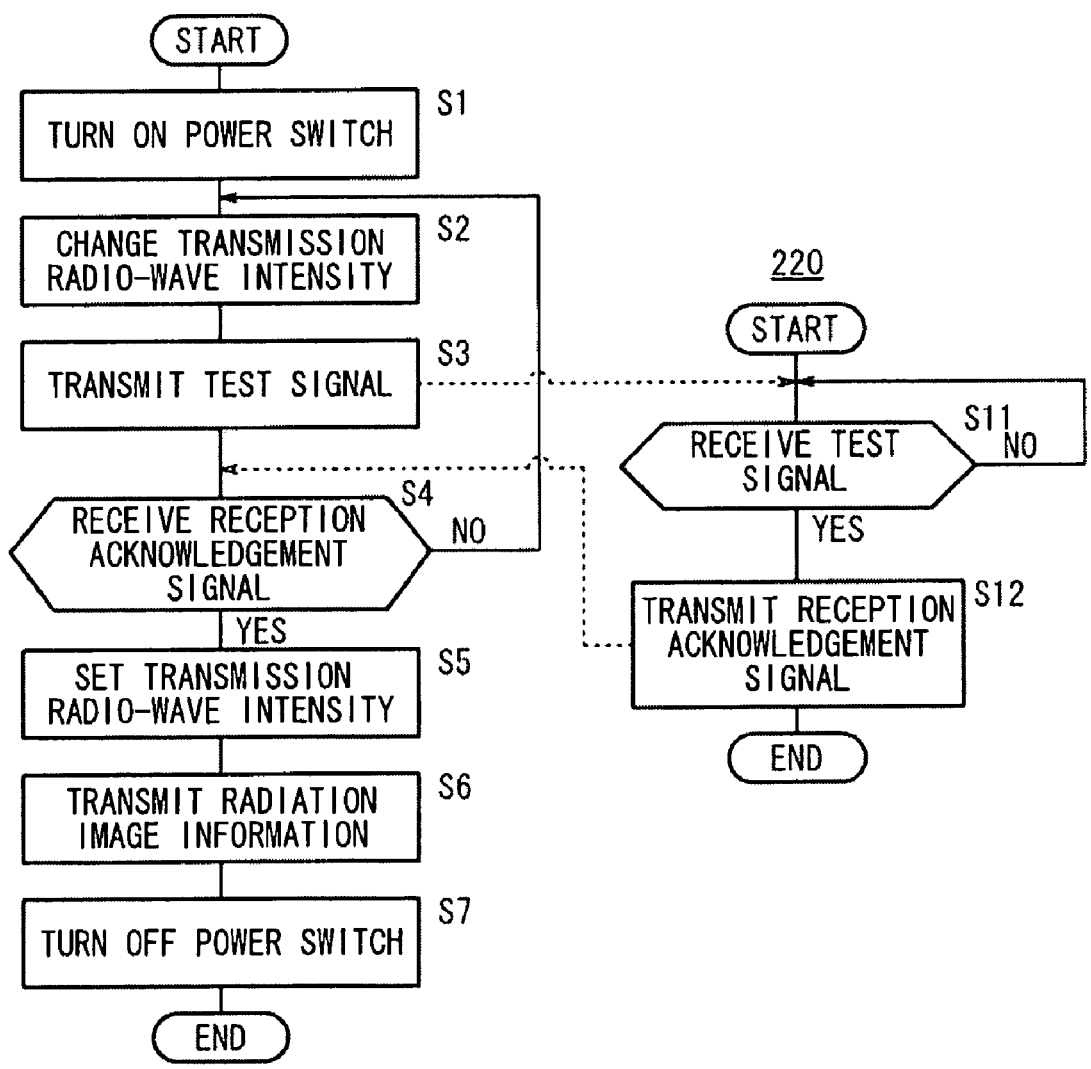
FIG. 6 is a flowchart of an operation sequence of the radiation image capturing system.

The radiation image capturing system 10 according to the present embodiment is basically constructed as described above, and operation of the radiation image capturing system 10 will be described below with reference to a flowchart shown in FIG. 6.

The radiation image capturing system 10 is installed in the operating room 12 and used when a radiation image of the patient 14 is required by the surgeons 18 who are performing an operation on the patient 14. Before a radiation image of the patient 14 is captured, patent information of the patient 14 to be imaged is registered in the patient information manager 102 of the console 28. If an area to be imaged of the patient 14 and an image capturing method have already been known, they are previously registered as image capturing conditions in the image capturing condition manager 98. After the above preparatory process is finished, the surgeons 18 perform an operation on the patient 14.

For capturing a radiation image of the patient 14 during the operation, one of the surgeons 18 or the radiological technician places the cassette 24 on a predetermined position between the patient 14 and the surgical table 16 with the irradiated surface 36 facing the image capturing apparatus 22, and turns on the power switch 45.

In step S1, the cassette transceiver controller 202 of the cassette transceiver 48 detects when the power switch 45 is turned on.

In step S2, the transmission radio-wave intensity changer 206 supplies the variable-gain amplifier 212 with a variable-gain control signal Sc for setting the transmission radio-wave intensity to a minimum level.

In step S3, the test signal generator 204 generates a test signal comprising a unique word and outputs the test signal to the transmitter 210. The test signal is supplied from the transmitter 210 to the variable-gain amplifier 212, which amplifies the test signal. The amplified test signal is supplied as a transmission signal St representing the minimum radio-wave intensity through the antenna sharing unit 205 to the antenna 203, which transmits the transmission signal St as a radio wave.

In step S4, a timing means (timer), not shown, monitors for a given period of time whether the cassette transceiver 48 has received a reception acknowledgement signal indicating that the console transceiver 96 has received the test signal or not.

If the cassette transceiver 48 has not received a reception acknowledgement signal within the given period of time in step S4, then the transmission radio-wave intensity changer 206 increases the transmission radio-wave intensity by a certain level, and the cassette transceiver 48 transmits a test signal at the increased transmission radio-wave intensity level as a transmission signal St. In this manner, unless the cassette transceiver 48 receives a reception acknowledgement signal, it transmits a test signal at a transmission radio-wave intensity level increased stepwise as a transmission signal St.

In step S11, the console transceiver controller 220 of the console transceiver 96 monitors at all times whether it has received a test signal or not.

If the console transceiver controller 220 confirms that it has received a test signal in step S11, the reception acknowledgement signal generator 232 generates a reception acknowledgement signal in step S12, and transmits the reception acknowledgement signal through the transmitter 230, the antenna sharing unit 226, and the antenna 224.

At this time, in step S4, the cassette transceiver controller 202 of the cassette transceiver 48 confirms the reception of the reception acknowledgement signal.

In step S5, the cassette transceiver controller 202 stores the variable-gain control signal Sc (the value thereof), representing its own transmission radio-wave intensity, which has been set in the variable-gain amplifier 212 at the time it has received the reception acknowledgement signal, in the transmission radio-wave intensity setting unit 207.

Consequently, when a signal radio wave representing radiation image information is transmitted from the cassette 24, the signal radio-wave intensity thereof is held to a minimum (required minimum), and the power consumption of the battery 44 of the cassette 24 is reduced.

The variable-gain control signal Sc (the value thereof) set in the transmission radio-wave intensity setting unit 207 may be the sum of the variable-gain control signal Sc (the value thereof) which has been set in the variable-gain amplifier 212 at the time it received the reception acknowledgement signal, and a certain value. In this manner, the cassette transceiver 48 is capable of reliably transmitting radiation image information while saving the electric power stored in the battery 44.

Then, after having moved the image capturing apparatus 22 to a position confronting the radiation detecting cassette 24, one of the surgeons 18 or the radiological technician turns on the image capturing switch 72.

When the image capturing switch 72 is turned on, the radiation source controller 78 of the image capturing apparatus 22 acquires the image capturing conditions with respect to the area to be imaged of the patient 14 from the image capturing condition manager 98 of the console 28 by way of wireless communications via the console transceiver 96 and the transceiver 76. The radiation source controller 78 controls the radiation source 74 to apply a radiation X at a given dose to the patient 14 according to the acquired image capturing conditions.

The radiation X which has passed through the patient 14 is applied to the grid 38, which removes scattered rays of the radiation X. Then, the radiation X is applied to the radiation detector 40, and converted into electric signals by the photoelectric conversion layer 51 of the pixels 50 of the radiation detector 40. The electric signals are stored as electric charges in the storage capacitors 53 (see FIG. 3). The stored electric charges, which represent radiation image information of the patient 14, are read from the storage capacitors 53 according to address signals which are supplied from the address signal generator 80 of the cassette controller 46 to the line scanning driver 58 and the multiplexer 66.

Specifically, in response to the address signal supplied from the address signal generator 80, the address decoder 60 of the line scanning driver 58 outputs a selection signal to select one of the switches SW1, which supplies the control signal Von to the gates of the TFTs 52 connected to the gate line 54 corresponding to the selected switch SW1. In response to the address signal supplied from the address signal generator 80, the address decoder 68 of the multiplexer 66 outputs a selection signal to successively turn on the switches SW2 to switch between the signal lines 56 for thereby reading radiation image information represented by the electric charges stored in the storage capacitors 53 of the pixels 50 connected to the selected gate line 54, through the signal lines 56.

The radiation image information (electric charges) read from the storage capacitors 53 of the pixels 50 connected to the selected gate line 54 are amplified by the respective amplifiers 62, sampled by the sample and hold circuits 64, and supplied to the multiplexer 66. Based on the supplied electric charges, the multiplexer 66 generates and supplies a radiation image signal to the A/D converter 70, which converts the radiation image signal into a digital signal. The digital signal which represents the radiation image information is stored in the image memory 82 of the cassette controller 46.

Similarly, the address decoder 60 of the line scanning driver 58 successively turns on the switches SW1 to switch between the gate lines 54 according to the address signal supplied from the address signal generator 80. The electric charges serving as radiation image information stored in the storage capacitors 53 of the pixels 50 connected to the successively selected gate lines 54 are read through the signal lines 56, and processed by the multiplexer 66 and the A/D converter 70 into digital signals, which are stored in the image memory 82 of the cassette controller 46.

In step S6, the radiation image information stored in the image memory 82 is read from the image memory 82 and transmitted to the console 28 at a minimum transmission radio-wave intensity level based on the variable-gain control signal Sc which has already been set in the control signal port of the variable-gain amplifier 212 through the transmission radio-wave intensity setting unit 207 via the cassette transceiver 48 by way of wireless communications, or at a transmission radio-wave intensity level close to the minimum transmission radio-wave intensity level.

The radiation image information transmitted to the console 28 is received by the console transceiver 96, processed by the image processor 100, and then stored in the image memory 101 in association with the patient information of the patient 14 registered in the patient information manager 102.

The radiation image information processed by the image processor 100 is transmitted from the console transceiver 96 to the display device 26. In the display device 26, the receiver 90 receives the radiation image information, and the display controller 92 controls the display unit 94 to display a radiation image based on the radiation image information.

When the completion of the transmission of the radiation image information is confirmed in step S6, the cassette transceiver controller 202 sends the switch control signal Ss to turn off the power switch 45. Therefore, the cassette 24 is prevented from being left in a standby mode in which a certain amount electric power is consumed with the power switch 45 being turned on. Thus, electrical power saving of the battery 44 is further facilitated.

In the radiation image capturing system 10 according to the present embodiment, the cassette 24 has the radiation detector 40 for detecting the radiation X that has passed through the patient 14 as a subject and converting the radiation X into radiation image information, the image memory 82 for storing the converted radiation image information, the cassette transceiver 48 as the first transceiver for changing the transmission radio-wave intensity at which the test signal or the radiation image information stored in the image memory 82 is transmitted to the external source by way of radio communications, and the battery 44 for supplying electric power to the radiation detector 40 and the cassette transceiver 48. The radiation image capturing system 10 has the console 28 as the external controller having the console transceiver 96 as the second transceiver for receiving the test signal and the radiation image information transmitted from the cassette 24 and transmitting the reception acknowledgement signal to the cassette transceiver 48.

When the cassette transceiver 48 of the cassette 24 starts transmitting the radiation image information to the console transceiver 96 of the console 28, the cassette transceiver 48 changes the gain of the variable-gain amplifier 212 stepwise from a minimum value to change the transmission radio-wave intensity, and transmits the test signal as the transmission signal St at the changed transmission radio-wave intensity. When the console transceiver 96 receives the transmission signal St as the test signal at the changed transmission radio-wave intensity, the console transceiver 96 transmits the reception acknowledgement signal generated by the reception acknowledgement signal generator 232 to the cassette transceiver 48. In response to the reception acknowledgement signal, the cassette transceiver 48 sets its own transmission radio-wave intensity to the value at the time it received reception acknowledgement signal, and transmits the radiation image information at the set transmission radio-wave intensity. Therefore, the power consumption for transmitting the radiation image information from the cassette transceiver 48 to the console transceiver 96 is minimized, and the electric power stored in the battery 44 of the cassette 24 is greatly saved.

When the cassette transceiver 48 receives the reception acknowledgement signal, it sets its own transmission radio-wave intensity to the value representing the sum of the transmission radio-wave intensity at the time it received the reception acknowledgement signal and a certain value, and transmits the radiation image information at the set transmission radio-wave intensity. Therefore, the cassette transceiver 48 can transmit the radiation image information stably and reliably while saving the electric power stored in the battery 44.

Inasmuch as the transmission signal St as the test signal is transmitted when the power switch 45 is turned on, the radiation image information can reliably be transmitted to the console transceiver 96 when the radiation image information is stored in the image memory 82 of the cassette 24. Since the power switch 45 is turned off when the transmission of the radiation image information is finished, the electric power stored in the battery 44 is further saved.

According to the present embodiment, the power consumption at the time the radiation image information is transmitted from the cassette 24 to the console 28 by way of wireless communications is held to a minimum required. Consequently, the electric power of the battery 44 for energizing the cassette 24 can be saved.

Figure 7:
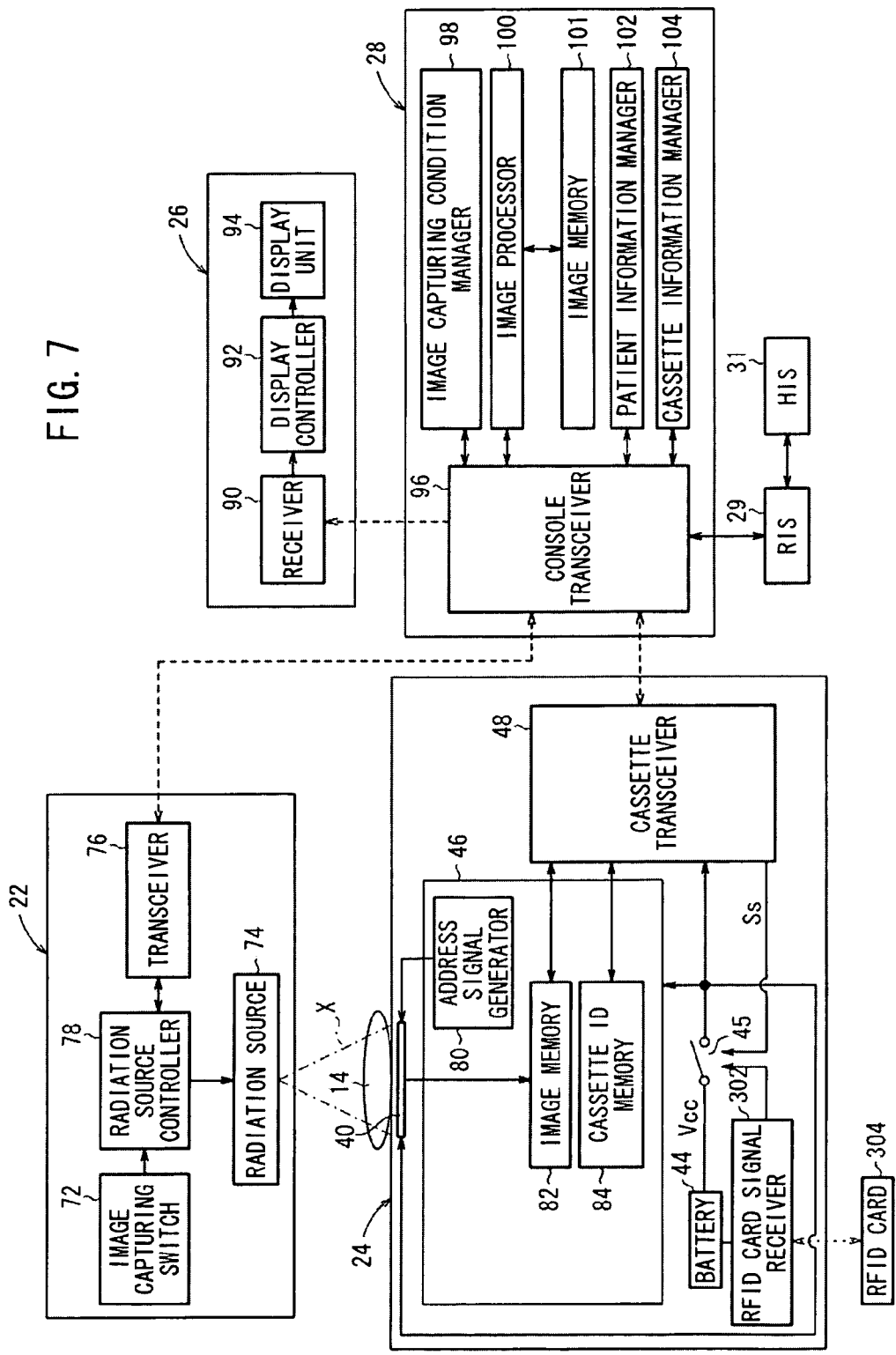
FIG. 7 is a block diagram of a radiation image capturing system according to another embodiment of the present invention.

Prior to starting to capture a radiation image of the patient 14, the power switch 45 may be turned on in step S1 by wireless communications when, as shown in FIG. 7, one of the surgeons 18 or the radiological technician holds an RFID (Radio-Frequency IDentification) card 304 certified for the identification thereof over an RFID card signal receiver (RFID transceiver) 302 on the cassette 24.

In the radiation image capturing system 10 according to the illustrated embodiment, the radiation detector 40 housed in the cassette 24 directly converts the dose of the applied radiation X into an electric signal with the photoelectric conversion layer 51. However, the radiation image capturing system 10 may employ a radiation detector including a scintillator for converting the applied radiation X into visible light and a solid-state detecting device such as of amorphous silicon (a-Si) or the like for converting the visible light into an electric signal (see Japanese Patent No. 3494683).

Alternatively, the radiation image capturing system 10 may employ a light-conversion radiation detector for acquiring radiation image information. The light-conversion radiation detector operates as follows: When a radiation is applied to a matrix of solid-state detecting devices, the solid-state detecting devices store an electrostatic latent image depending on the dose of the applied radiation. For reading the stored electrostatic latent image, reading light is applied to the solid-state detecting devices to cause the solid-state detecting devices to generate an electric current representing radiation image information. When erasing light is applied to the radiation detector, radiation image information representing a residual electrostatic latent image is erased from the radiation detector, which can thus be reused (see Japanese Laid-Open Patent Publication No. 2000-105297).

When the cassette 24 is used in the operating room 12 or the like, the cassette 24 may be subjected to adhesion of blood, contamination, etc. However, when the cassette 24 is designed to have a waterproof and hermetically-sealed structure, and is sterilized and cleaned as necessary, one cassette 24 can be used repeatedly.

The cassette 24 is not limited to use in the operating room 12, and may be used for a medical examination and a round in the hospital.

Also, the cassette 24 may communicate with external devices via optical wireless communication using infrared light or the like, instead of general wireless communication using radio wave.

Figure 8:
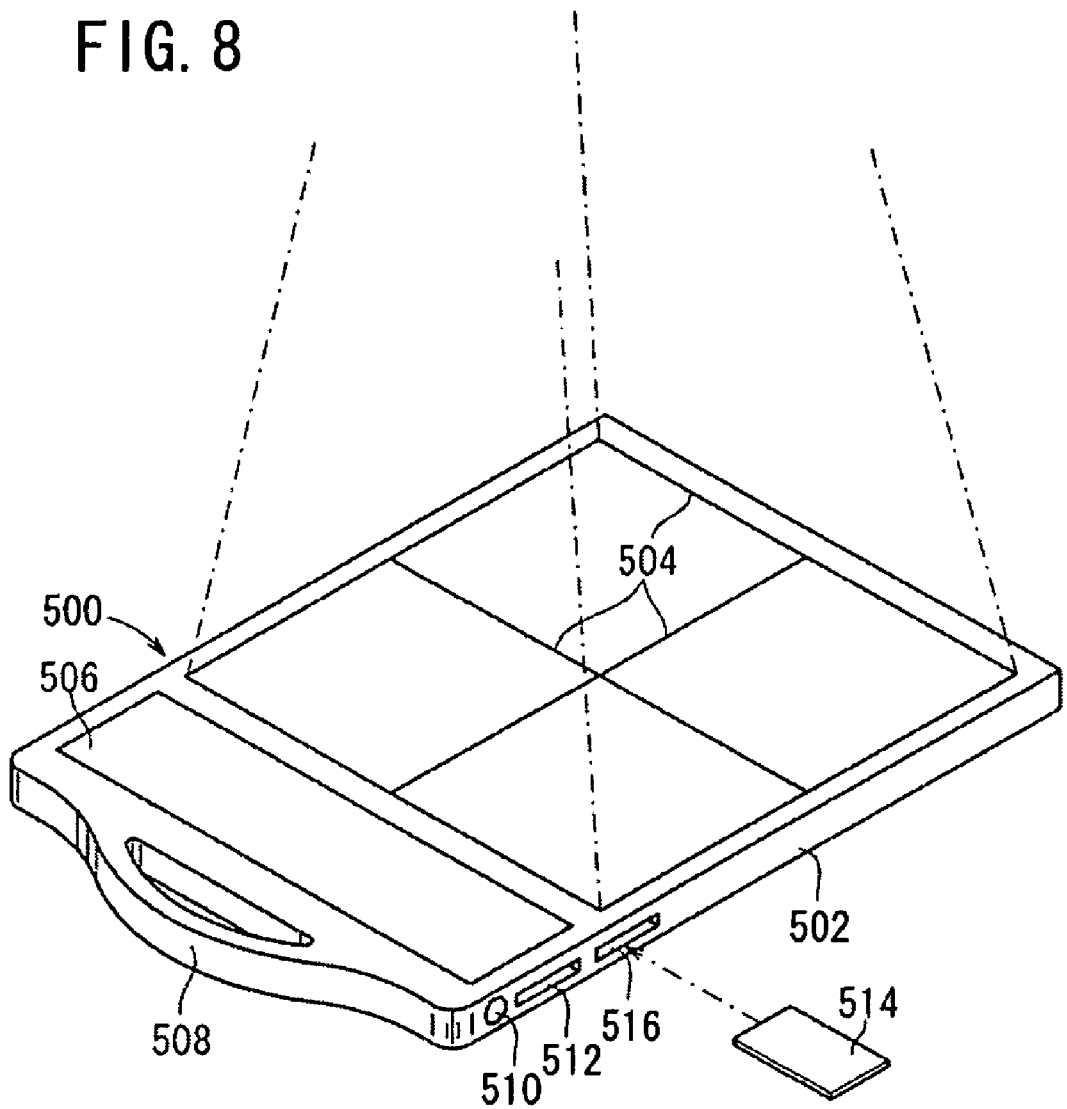
FIG. 8 is a perspective view showing a radiation detecting cassette in the radiation image capturing system according to another embodiment of the present invention.

Preferably, the cassette 500 may be constructed as shown in FIG. 8.

Specifically, the cassette 500 includes a guiding line 504 drawn on the radiation-irradiated surface of a casing 502, the guiding line 504 serving as a reference for setting a captured area and a captured position. Using the guiding line 504, a subject such as a patient 14 can be positioned with respect to the cassette 500, and an area irradiated with radiation X can be set, thereby recording radiation image information on an appropriate captured area.

The cassette 500 is provided with a display section 506 on an area thereof other than the captured area, for displaying various information about the cassette 500. The information which is displayed on the display section 506, includes ID information of a subject such as a patient 14 whose radiation image information is to be recorded on the cassette 500, the number of times the cassette 500 has been used, an accumulated exposed radiation dose, a charging state (remaining battery level) of a battery 44 in the cassette 500, image capturing conditions of radiation image information, and a positioning image of the subject such as the patient 14 with respect to the cassette 500. In this case, a technician confirms a subject such as a patient 14 based on the ID information displayed on the display section 506, for example, and also previously confirms that the cassette 500 is placed in a usable state. Then, the technician positions a desired captured area of the subject such as the patient 14 with respect to the cassette 500 based on the displayed positioning image, thereby capturing appropriate radiation image information.

Also, the cassette 500 is provided with a handgrip 508, whereby it is easier to handle and carry the cassette 500.

Preferably, the cassette 500 may have, on a side thereof, an input terminal 510 for an AC adapter, a USB (Universal Serial Bus) terminal 512, and a card slot 516 for inserting a memory card 514.

When the charging function of the battery 44 in the cassette 500 becomes deteriorated, or when there is not enough time to fully charge the battery 44, the input terminal 510 is connected to the AC adapter to externally supply the cassette 500 with electric power, thereby enabling the cassette 500 to be used immediately.

The USB terminal 512 or the card slot 516 may be used when the cassette 500 cannot transmit and receive information to and from external devices such as the console 28 via wireless communication. Specifically, by connecting a cable to the USB terminal 512, the cassette 500 can transmit and receive information to and from the external devices via wire communication. Alternatively, the memory card 514 is inserted into the card slot 516, and necessary information is recorded on the memory card 514. After that, the memory card 514 is removed from the card slot 516, and the memory card 514 is inserted into the external device, thereby enabling information to be transferred.

Figure 9:
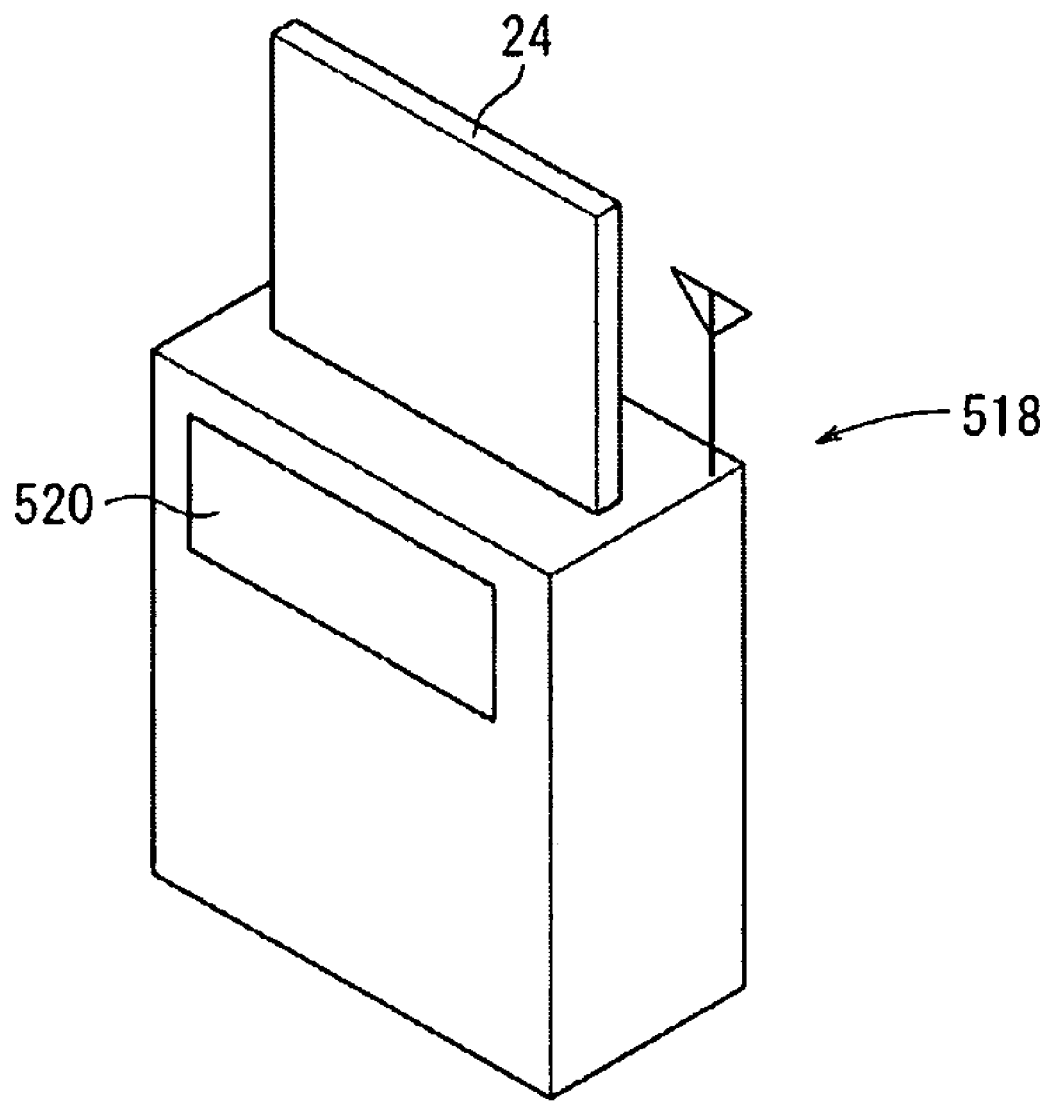
FIG. 9 is a perspective view showing a cradle which charges the radiation detecting cassette.

Preferably, a cradle 518 may be disposed in the operating room 12 or at a desired place in the hospital, into which the cassette 24 is inserted to charge the internal battery 44, as shown in FIG. 9. In this case, in addition to charging the battery 44, the cradle 518 may transmit and receive necessary information to and from external devices such as HIS 31, RIS 29, the console 28, etc. by way of wireless or wire communications of the cradle 518. The information may include radiation image information which is recorded on the cassette 24 inserted into the cradle 518.

Also, the cradle 518 may be provided with a display section 520. The display section 520 may display necessary information including a charging state of the inserted cassette 24 and radiation image information acquired from the cassette 24.

Further, a plurality of cradles 518 may be connected to a network. In this case, information about charging states of cassettes 24 inserted in respective cradles 518 can be collected through the network, and the cassette 24 in a usable state can be located.

As shown in FIG. 10, the battery 44 of the cassette 24 is directly connected to the cassette transceiver 48 which has a sleep and wake-up function, and supplies standby electric power (low electric power) to the cassette transceiver 48 when it is in a sleep mode.

Accordingly, the power supply switch 45 of the cassette 24 is turned on by the switch control signal Ss output in response to a turn-on command transmitted from the external controller 28 via the second transceiver 96. When the transmission of the radiation image information is finished, because the cassette transceiver 48 is supplied with the standby electric power, the cassette 24 can be adapted to turn off the power supply switch 45 by the switch control signal Ss. Although certain preferred embodiments of the present invention have been shown and described in detail, it should be understood that various changes and modifications may be made therein without departing from the scope of the appended claims.

What is claimed is:

1. A radiation image capturing system comprising:
a cassette comprising a radiation detector for detecting a radiation having passed through
a subject and converting the detected radiation into radiation image information, an image
memory for storing the converted radiation image information, a first transceiver for changing a transmission radio-wave intensity at which a test signal or the radiation image information stored in said image memory is transmitted to an external source by way of wireless communications, a battery for supplying electric power to said radiation detector and said first transceiver, and a power switch; and
an external controller comprising a second transceiver for receiving the test signal and the radiation image information transmitted from said cassette and transmitting a reception acknowledgement signal to said first transceiver;
wherein said power switch is turned on
in response to a turn-on command transmitted from said external controller via said second transceiver and then said first transceiver transmits said test signal while changing the transmission radio-wave intensity, and when said second transceiver receives said test signal, said second transceiver transmits said reception acknowledgement signal, and in response to said reception acknowledgement signal, said first transceiver sets a transmission radio-wave intensity of its own to a value at the time said first transceiver received said reception acknowledgement signal, and transmits the radiation image information at the set transmission radio-wave intensity.

2. A radiation image capturing system according to claim 1, wherein when said first transceiver receives said reception acknowledgement signal, said first transceiver sets a transmission radio-wave intensity of its own to a value which represents the sum of the transmission radio-wave intensity at the time said first transceiver received said reception acknowledgement signal and a predetermined value, and transmits the radiation image information at the set transmission radio-wave intensity.

3. A radiation image capturing system according to claim 1, wherein when the transmission of the radiation image information is finished, under a condition where said first transceiver is supplied with a standby electric power, said cassette turns off said power supply switch.

4. A radiation image capturing system according to claim 3, wherein said cassette further comprises an RFID card signal receiver for turning on said power switch when a certified RFID card is held over said RFID card signal receiver.

5. A radiation image capturing system according to claim 1, wherein said cassette turns off said power switch when said first transceiver finishes transmitting the radiation image information with said power switch being turned on.

6. A radiation image capturing system according to claim 1, further comprising:
an image capturing apparatus for applying said radiation at a dose according to image capturing conditions to said subject;
wherein said external controller comprises a console for supplying said image capturing conditions to said image capturing apparatus.

7. A radiation image capturing system according to claim 6, wherein said console supplies said image capturing conditions to said image capturing apparatus via said second transceiver by way of wireless communications.

* * * * *